United States Patent [19]

Takahashi et al.

[11] Patent Number: 5,624,685
[45] Date of Patent: Apr. 29, 1997

[54] HIGH POLYMER GEL AND VASCULAR LESION EMBOLIZING MATERIAL COMPRISING THE SAME

[75] Inventors: Toru Takahashi, Shizuoka-ken; Hideki Nakamura, Kanagawa-ken; Katsuya Goto, Fukuoka-ken, all of Japan

[73] Assignee: Terumo Kabushiki Kaisha, Tokyo, Japan

[21] Appl. No.: 416,530

[22] Filed: Apr. 3, 1995

Related U.S. Application Data

[63] Continuation of Ser. No. 961,519, Oct. 15, 1992, abandoned.

[30] Foreign Application Priority Data

Oct. 16, 1991 [JP] Japan ................................. 3-267540

[51] Int. Cl.$^6$ .......................... A61K 47/36; A61K 47/32; A61M 25/04
[52] U.S. Cl. .......................... 424/488; 424/487; 424/484; 252/315.3; 252/315.4; 514/944
[58] Field of Search ........................ 424/484, 488, 424/9.4, 9.5, 485, 451, 455; 252/315.3, 315.4; 524/916; 514/944

[56] References Cited

U.S. PATENT DOCUMENTS

| | | | |
|---|---|---|---|
| 3,640,741 | 2/1972 | Etes | 424/401 |
| 3,850,838 | 11/1974 | Guckenberger et al. | 514/779 |
| 4,347,261 | 8/1982 | Challen et al. | 426/573 |
| 4,393,048 | 7/1983 | Mason, Jr. et al. | 424/132 |
| 4,401,456 | 8/1983 | Connick, Jr. | 424/488 |
| 4,501,834 | 2/1985 | Su | 524/28 |
| 4,795,741 | 1/1989 | Leschiner et al. | 514/21 |
| 4,948,575 | 8/1990 | Cole et al. | 424/44 |
| 5,144,016 | 9/1992 | Skjak-Braek et al. | 536/3 |
| 5,356,654 | 10/1994 | Speirs et al. | 426/575 |

*Primary Examiner*—Edward J. Webman
*Attorney, Agent, or Firm*—Burns, Doane, Swecker & Mathis, LLP

[57] ABSTRACT

The improved vascular lesion embolizing material comprises a high-polymer gel capable of absorbing water in an amount of 10 ml/g and more. The high-polymer gel is preferably such as is produced by first permitting a solution containing a water-soluble high polymer to be precipitated in a solution containing polyvalent cation, said high polymer having a plurality of monovalent anionic functional groups, and then immersing the resulting precipitate in a salt solution. The material will swell upon contact with blood and is capable of embolizing a focal lesion in a blood vessel without causing any adverse effects on the living body. The swell time can be shortened if the embolizing material is made of a high-polymer gel that has been treated with a salt solution after precipitation.

10 Claims, 3 Drawing Sheets

HIGH POLYMER GEL AND VASCULAR LESION EMBOLIZING MATERIAL COMPRISING THE SAME

This application is a continuation of Application Ser. No. 07/961,519, filed Oct. 15, 1992 abandoned.

BACKGROUND OF THE INVENTION

1. Field of the Invention

This invention relates to a high-polymer gel and a blood vessel obstructing material comprising the same. More particularly, this invention relates to a vascular lesion embolizing material that can advantageously be used for the treatment of vascular lesions such as aneurysms and arteriovenous malformations (AVM).

2. Prior Art

In order to increase the number of successful cases in the treatment of cerebrovsacular lesions such as a large arteriovenous malformation which is difficult to access anatomically and a large aneurysm which defies surgical operations or which is amenable to surgical operations only with much difficulty, and for the purpose of reducing the physical, mental and economic burdens on patients, there has recently been a great enthusiasm for intravascular surgical treatments which are conducted using intravascular catheters without casing stresses due to surgical operations (Katsuya Goto, Neurosurgeons 9, 229–239, 1990).

In the case of treatment of a cerebrovascular disorder, a very small catheter is inserted superselectively into the affected site of a cerebral artery and an embolizing substance is supplied through the catheter so as to obstruct a cerebral aneurysm, an arteriovenous malformation, an arteriovenous fistula, and the like.

The blood vessels of the brain are different from the blood vessels in other parts of the human body in that they lack an outer elastic membrane and that they have thin walls; therefore, they are less resistant to the lateral pressure of blood streams. Furthermore, blood vessels run in a complex way within the skull and, in particular, patients suffering from hypertension tend to experience disorders under stresses acting on branches. Autopsy statistics teaches that in one out of a hundred adult cases, cerebral aneurysms occur in the arteriovenous system; they have a wide morphological distribution ranging in diameter from about 1 mm to about 20 mm and more, with the site of their occurrence centering on the circle of Willis but distributed widely among cerebral arteries. If cerebral aneurysms rupture, they will cause serious cerebrovascular disorders such as subarachnoid hemorrhage and intracerebral hemorrhage; if they grow in size excessively, they will cause a symptom of compressed cranial nerves. An arteriovenous malformation is the most common and best known of cerebravascular malformations and it consists of an aggregate of meandering or dilated blood vessels to and from the brain and intervening blood vessels that have arteriovenous anastomosis. Clinically, areteriovenous malformations are important as a cause of intracerebral hemorrhage, subarachnoid hemorrhage, epilepsy and progressive neurofunction loss that are manifested in fairly young patients.

Embolization is a technique that is intended to treat the cerebral arterial lesions described in the preceding paragraphs by obstruction with embolizing substances so that the blood stream in the lesion is suspended to coagulate the affected part. If necessary, the coagulated part may be removed.

The embolization technique has come to play a central part in the treatment of cerebral arteriovenous malformations (Goto, K. et al., Neuroradiology 33 (Supple) 193–194, 1991) and so will it be in the treatment of cerebral aneurysms in the near future (Katsuya Goto, Igaku no Ayumi (Advances in Medicine) 153: 653, 1990).

Cyanoacrylate base materials have heretofore been used as common liquids for obstructing sites of vascular lesions (J. Biomed. Mater. Res., 17, 167–177 (1983) by M. C. Harpers et al.).

It has recently been proposed that a solution of an ethylene=vinyl alcohol copolymer (EVAL®) in dimethyl sulfoxide (DMSO) be used as an embolizing material so that DMSO is diffused in blood to obstract a blood vessel by precipitating EVAL® (Medical Tribune, Oct. 26, 1989, pp. 46–47).

Another method that is practiced today is to used a balloon (detachable balloon) that can be cut off within an aneurysm; the balloon is inserted into the aneurysm, blown to obstruct it using a catheter and thereafter detached to be retained in it (Journal of Neurosurgery, 41, 125–145 (1974) by F. A. Serbinenko).

Metal coils (minicoils), polyvinyl alcohol (PVA) sponges, alcohols, sutures, etc. have also been used in accordance with the specific objective of treatment.

The conventional embolizing materials and methods, however, have various problems. First, the cyanoacrylate base embolizing substances are difficult to inject into blood vessels since they will rapidly solidify to polymerize. In order to insure that a catheter will not be pasted to the inner surface of a blood vessel in the brain on account of the strong bonding action of the embolizer, the catheter must be pulled out of the sheath as quickly as possible after injection of the embolizer ends. This adds to the difficulty encountered with handling of the conventional cyanoacrylate base embolizing substances, and even if occlusion of the blood vessel by first injection is found to be inadequate, second injection is impossible. A further problem with these embolizing substances is that their irritating action on the wall of a blood vessel is strong enough to potentially cause an intense inflammatory reaction.

The system having EVAL® dissolved in solvent DMSO has the problem that the solvent will linger in the central part of EVAL® that has precipitated upon contact with running blood. In the case where the system is used for embolization of an arteriovenous malformation, the substance that has precipitated within the blood vessel tends to be disrupted into small pieces by turbulent flows of the blood, which will be carried away in veins coming out of the brain. If the system is used for embolization of an aneurysm, the part of the precipitate that projects beyond the exit of the aneurysm stream in the Y-shaped branch of a blood vessel as shown schematically in FIG. 2.

As a further problem, DMSO is not an ideal solvent since its safety has not yet been established (Hiroo Iwata et al., Preprint for the 11th Meeting of the Society of Biomaterials of Japan, 68, II—22, 1989) and, in addition, it can do harm to apparatuses that are made of plastics.

A detachable balloon is frequently used in embolization of aneurysms. However, because of the weak reaction between the balloon and the inner surface of the aneurysm, the cavity in the aneurysm might not be completely filled with the balloon and no matter how small the unfilled lumen may be, there is a high risk of the recurrence of the aneurysm. If it is attempted to fill the lumen as much as possible by maximizing the inflation of the balloon, the pressure buildup in the latter will alter the shape of the aneurysm, increasing the change of its rupture. As a further problem, a tractive force must be applied to detach the balloon from the catheter but this again increases the chance of the rupture of the aneurysm.

The state-of-the-art technology of embolization is such that it is difficult to block the neck of the aneurysm completely even if a detachable balloon or a minicoil is used and proximal obstruction (part of the parent artery is obstructed) is more often practiced (Akira Takahashi, Igaku no Ayumi (Advances in Medicine), 154, (7), 432, 1990). However, this method unavoidably sacrifices the parent artery, exposing the brain to the danger of a blood stream disorder. It has been proposed that a detachable balloon be used in combination with minicoils for embolization of a large aneurysm (Katsuya Goto, Abstracts of the IVR Study Group of Angiography, Japan, 1991); however, this method requires many expensive minicoils, takes much time and yet it is incapable of achieving the intended evacuation.

Other conventional embolizing materials such as PVA granules, alcohols and satures are not only difficult to handle, they also have many problems in association with treatment such as insufficient therapeutic effects.

SUMMARY OF THE INVENTION

The present invention has been accomplished under these circumstances and has as an object providing a vascular lesion embolizing material that is easy to handle, that will no be disrupted into small pieces to be carried in to a blood vessel, and that is free from unwanted side effects of solvents.

This object of the present invention can be attained by a high-polymer gel that is produced by first permitting a solution containing a water-soluble high polymer to be precipitated in a solution containing a polyvalent cation, said high polymer having a plurality of monovalent anionic functional groups, and then immersing the resulting precipitate in a salt solution.

At least one solution selected from the group consisting of the solution containing a water-soluble high polymer, the solution containing a polyvalent cation and the salt solution may further contain a blood coagulating substance and/or an X-ray contrast medium.

In a preferred embodiment, the high-polymer gel may be such that the water-soluble high polymer is an alkali metal salt of alginic acid, the polyvalent cation being a calcium ion and the salt solution being an aqueous solution of a sodium salt.

The object of the present invention can also be attained by a vascular lesion embolizing material that comprises a high-polymer gel capable of absorbing water in an amount of 10 ml/g and more.

The high-polymer gel may be bound with a binder or confined in a capsule.

DETAILED DESCRIPTION OF THE INVENTION

Figure 1:
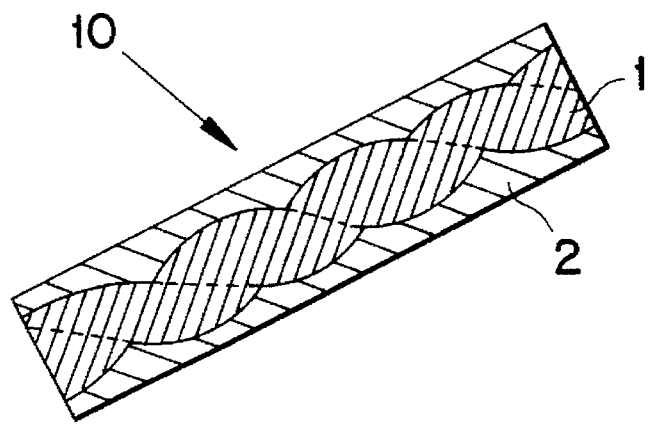
FIG. 1 is a cross-sectional view showing a preferred example of the vascular lesion embolizing material of the present invention.

The features of the present invention are described below in detail. The vascular lesion embolizing material of the present invention comprises a high-polymer gel capable of absorbing water in an amount of 10 ml/g and more. When the high-polymer gel which is capable of absorbing water in an amount of 10 ml/g and more is supplied, either as such or after bound with a binder or confined in a capsule, to the site of a blood vessel having a lesion to be repaired or its neighborhood, the gel swells upon contact with blood and spreads readily in the blood vessel to close the lumen of the blood vessels with lesion. If the high-polymer gel absorbs water in an amount less than 10 ml/g, it will not swell sufficiently upon contact with blood to close the blood vessel completely.

The high-polymer gel to be used in the present invention is not limited in any way except that it should be capable of absorbing water in an amount of at least 10 ml/g. However, it is preferred to use the high-polymer gel that is described below and which is also claimed by the present invention. This high-polymer gel is produced by first permitting a solution containing a water-soluble high polymer to be precipitated in a solution containing a polyvalent cation, said high polymer having a plurality of monovalent anionic functional groups, and then immersing the resulting precipitate in a salt solution. In the presence of a polyvalent cation such as a polyvalent metal ion, the monovalent anionic functional groups in the high polymer will surround said cation and bind with it to either solidify or form a gel substance on account of the complexation or crosslinking reaction of the high polymer. Preferably, the monovalent anionic functional groups are carboxyl groups since they will react with the polyvalent cation at a higher rate.

Examples of the water-soluble high-polymer having a plurality of monovalent anionic functional groups include: polysaccharides such as aliginic acid, carboxymethyl cellulose and acetyl cellulose, as well as alkali metal salts thereof; polypeptides such as polyglutamic acid and biopolymers thereof; and synthetic polymers such as polyacrylic acid, esters thereof, polymethacrylic acid and copolymers thereof.

When preparing solutions containing the above-described water-soluble high polymer, hydrophilic solvents such as water, alcohols and carboxylic acids are used. If the concentration of the water-soluble high-polymers in the solvents is adjusted to 0.1–10 wt. %, good handling is achieved in various operations including injection and transportation and, in addition, the desired gel substance can be formed in a satisfactory way.

The polyvalent cations that can be used include not only polyvalent metal ions such as $Ca^{++}$, $Mg^{++}$, $Ba^{++}$ and $Sr^{++}$ but also "polycations" such as chitosan and polyacrylamide.

When preparing solutions containing these polyvalent cations, hydrophilic solvents such as water, alcohols and carboxylic acids are used. If the concentration of the polyvalent cations in the solvents is adjusted to 0.1–10 wt %, the intended gel substance can be formed in a satisfactory way. The polyvalent cations are made into solution using metal chlorides or polymers in a solid or powder form.

The water-soluble high polymers may be combined with the polyvalent cations in various ways, as exemplified by the combination of sodium alginate with $Ca^{++}$, $Ba^{++}$, $Sr^{++}$, or chitosan, the combination of carboxymethyl cellulose with chitosan, and the combination of poly (sodium acrylate) with $Ca^{++}$, $Ba^{++}$, $Mg^+$ or chitosan.

A particularly preferred combination of the solutions of water-soluble high polymer and polyvalent cation is a two-part system consisting of an aqueous solution of alkali metal alginate and an aqueous solution of a polyvalent metal ion. It is known that an alkali metal alginate and a polyvalent metal ion, when mixed together, will undergo an ion-exchange reaction to form an insoluble metal salt, thereby turning into a gel which can be used in spinning fibers (see Yoshio Kobayashi, Journal of the Society of Fiber Science & Technology, Japan, 46, (5), 202–205, 1990).

The alkali metal alginate is preferably a sodium salt and the polyvalent metal ion is preferably a calcium ion. Sodium alginate is preferably produced by the following method, which is given here for merely illustrative purposes and is in no way limiting: crude sodium alginate is extracted from brown algae in the form of a water soluble salt with alkali, then the extract is purified by precipitating the alginate in the form of a free acid or Ca salt by addition of a mineral acid or $CaCl_2$.

The gel produced by mixing the solutions of an alkali metal alginate and a polyvalent metal ion is known to be highly safe, have good biocompatibility and have such a characteristic that the greater part of it will be excreted within a short time even if it is not effectively utilized in vivo (see Yoshio Kobayashi, Tanpakushitsu Kakusan Koso (Protein, Nucleic Acid and Enzyme), 31, (11), 1066–1077, (1986).

The high-polymer gel thus produced may be washed as such with a suitable cleaner such as water, dried as appropriate and processed into a suitable form, such as thin strands, that can be used as vascular lesion embolizing material. However, it takes a prolonged time for the dried product to revert to a gel substance upon reabsorbing water. Hence, the present inventors conducted studies in order to develop an appropriate method for the post-treatment of the precipitating high-polymer gel and found that when the precipitating gel was dried after immersion in a salt solution, it would revert to a gel substance within a short time upon reabsorption of water.

The salt solution to be used for this purpose may be exemplified by a solution of an alkali metal salt which is preferably an aqueous solution of sodium chloride, more preferably a physiological saline solution (0.9% NaCl in aqueous solution). The high-polymer gel that is immersed in the salt solution after it has precipitated out may be dried and yet it will absorb water again to be reverted to the initial gel substance within a short time.

The high-polymer gel of the present invention may be used as dissolved in a solution that is capable of blood coagulation by itself; alternatively, a blood coagulating property may be imparted to at least one of the solution of the water-soluble high polymer, the solution of the polyvalent cation and the salt solution, or an X-ray contrast medium or a therapeutic drug may be added to at least one of those solutions.

An Exemplary method for imparting a blood coagulating property is to add a blood coagulation factor such as a fibrinogen, thrombin or calcium ion to either one or more of the solution of the water-soluble high-polymer, the solution of the polyvalent cation and the salt solution. If the high-polymer gel of the present invention is used as a vascular lesion embolizing material after it has been provided with a blood coagulating property, the coagulation of blood at the site of the vascular lesion is promoted, thereby enhancing the therapeutic efficacy of the material.

A compound that can be dissolved or dispersed in the solvent for the solution of water-soluble high polymer, the solution of polyvalent cation or the salt solution and which is commonly used in angiography may be used as an X-ray contrast medium that is mixed with at least one of the solutions mentioned above. Examples of such X-ray contrast media are water-soluble iodine-containing compounds including amidotrizoic acid, iothalamic acid, metrizoic acid, metrizamide, ioxaglic acid and iopamidol. These compounds are preferred since they will neither allow the solution of water-soluble high-polymer to gel independently of other solutions nor embrittle the resulting gel.

The high-polymer gel capable of absorbing water in an amount of 10 ml/g and more may immediately be used as a vascular lesion embolizing material. Preferably, the gel is shaped into any form that permits it to be easily introduced into the living body by a suitable means such as a catheter. To this end, the gel may be shaped into a short thread as shown in FIG. 1 using a binder; in FIG. 1, the gel is indicated by 1, the binder indicated by 2 and the embolizing material of the present invention by 10. The gel may be shaped into any other form that permits it to be easily inserted into a blood vessel by a suitable means such as a catheter; for example, the gel may be particulate, rod-shaped, in a sheet form, spherical, elliptical of fusiform. If desired, the high-polymer gel may be confined in a capsule or it may be knitted or twisted by itself, the two methods may be combined as appropriate.

The binder is preferably such that it dissolves readily in blood and may be exemplified by polysaccharides or oligosaccharides such as dextran, pullulan, hyaluronic acid and lactose, monosaccharides such as glucose and mannitol, and water-soluble substances such as proteins and water-soluble high polymers.

Movement within a catheter can be greatly facilitated if the high-polymer gel is shaped into a short thread that has a diameter or 3 mm and below, preferably 1 mm and below, more preferably 0.5 mm and below.

The vascular lesion embolizing material formed is preferably of such a shape that it can pass through a tube lumen having an inside diameter of 3 mm or less, more preferably 1 mm or less. The binders mentioned above may be used either independently or in suitable combinations so that the swelling of the high-polymer gel within the catheter is suppressed or retarded by a sufficient degree to facilitate its manipulation within the catheter. If the high-polymer gel is formed in this manner, it can be easily passed through a fine catheter and as it is retained in blood as a vascular lesion embolizing material, the binder will dissolve out and the gel will spread or swell sufficiently to close the blood vessel at the focus of the lesion.

Figure 2:
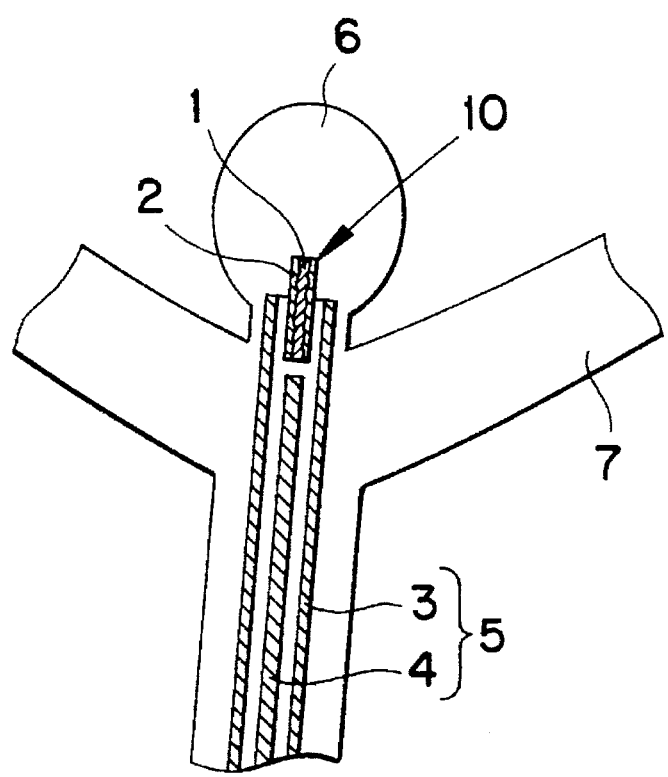
FIG. 2 is a diagram showing schematically the vascular lesion embolizing material of the present invention as it is inserted into a blood vessel.

We now describe the method of obstructing the blood stream at the focus of the lesion using the vascular lesion embolizing material of the present invention. FIG. 2 is a diagram showing schematically the focus of the lesion having an aneurysm 6 formed at the Y-shaped branch of a blood vessel 7.

To begin with, a catheter 5 is inserted into the blood vessel 7 in such a way that the tip of the catheter is directed to the interior of the aneurysm 6. The vascular lesion embolizing material 10 of the present invention is supplied into a catheter tube 3, pushed toward its distal end by manipulating a guide wire 4 and retained within the aneurysm 6. More than one embolizing material 10 may be used and the shape and the number of embolizing materials should be selected appropriately depending upon the size and shape of the aneurysm 6. After the embolizing material 10 is retained in the aneurysm 6, the catheter 5 consisting of the tube 3 and the guide wire 4 is withdrawn from the blood vessel.

Using a guide wire is not the sole method of transporting the embolizing material through the catheter and another method that can be used consists of feeding a priming solvent through the catheter by a suitable means such as a syringe so that the embolizing material is transported under the developing pressure until it is retained in position. A priming solvent may be a mixed system of water and ethanol or an X-ray contrast medium such as a water-soluble iodine-containing compound; using such solvents is effective in preventing the swelling of the high-polymer gel or the dissolution of the binder or capsule.

When the vascular lesion embolizing material of the present invention contacts blood, the binder covering its surface or the capsule will dissolve out or the priming solvent will disperse and the high-polymer gel 1 starts to swell and spreads readily within blood to close the lumen of the aneurysm 6.

The swollen gel substance will neither dissolve in blood nor exert an undue pressure on the aneurysm 6; hence, the interior of the aneurysm 6 can be occluded completely and safely by using the vascular lesion embolizing material 10 of the present invention.

The high-polymer gel of the present invention has another advantage in that compared to a superabsorbent resin typically made of a polyacrylate gel, it will swell effectively in both physiological saline and blood without being affected by the concentration of salt in solution.

Furthermore, the catheter 5 can be withdrawn easily without requiring any cumbersome technique such as applying an undue force.

If the embolizing material has a blood coagulating property or contains an X-ray contrast medium or a therapeutic drug, such property or component is kept within the swollen high-polymer gel, which is effective in causing an in vivo reaction (clot formation) to coagulate the blood or permitting X-ray monitoring or therapeutic treatment.

The present invention is described below in greater detail with reference to examples based on an aneurysm model. It should, however, be noted that the embolizing material of the present invention would also be advantageous for treating arteriovenous malformations.

EXAMPLE 1

Sodium alginate (0.2 g) was dissolved in distilled water (10.0 ml) to form a 2.0 w/v % aqueous solution. The solution was supplied into a syringe fitted with a 25G needle (i.d. 0.32 mm). The tip of the needle was dipped into an aqueous solution of calcium chloride having a concentration of 0.1 mol/L and the aqueous solution of sodium alginate was extruded into the $CaCl_2$ solution to precipitate a high-polymer gel.

After extrusion, the gel was kept immersed for 3 min in the aqueous solution of calcium chloride; thereafter, the strands of precipitating high-polymer gel were transferred into physiological saline, where they were kept immersed for 5 min.

The resulting high-polymer gel was fixed and dried in an oven (40° C.) for 20 min to yield threads of dried gel having an outside diameter of 74 μm.

It was verified that when the dried gel was dipped in physiological saline, it absorbed water and took only 2 min to swell to a size 7 times as large in outside diameter as the initial value. The dried gel thus obtained was capable of absorbing water in an amount of 28 ml/g.

Ten pieces of the dried gel each being 6 mm in length were set in a metal pipe (o.d. 0.4 mm; i.d. 0.3 mm; L 1.0 mm) as they were aligned to lie in the same plane at one end; thereafter, the gel pieces were fixed with a quick setting adhesive to prepare a vascular lesion embolizing material.

EXAMPLE 2

Figure 3:
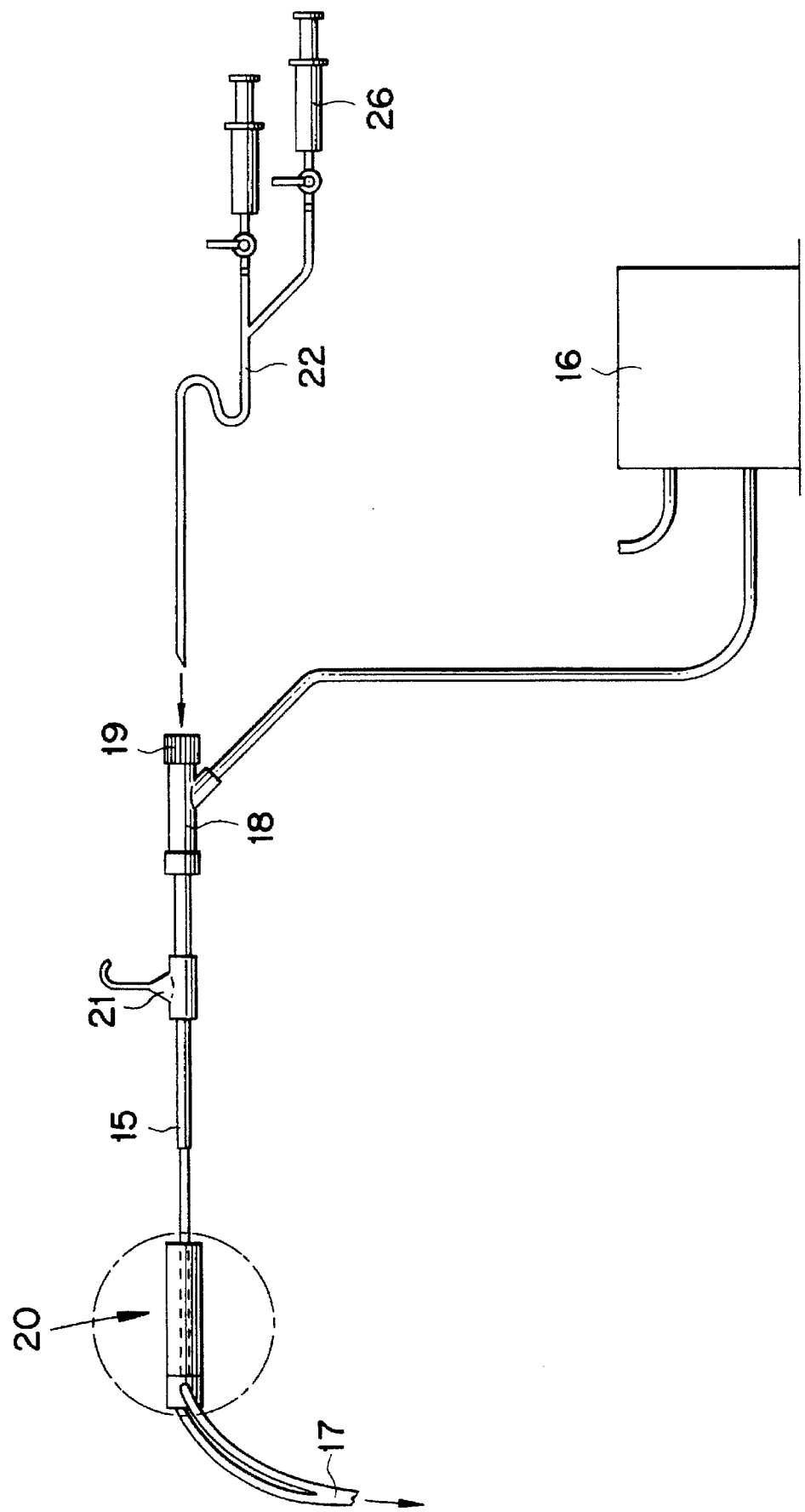
FIG. 3 is a diagram showing schematically the experimental system used in Examples 1 and 2 of the present invention.
Figure 4:
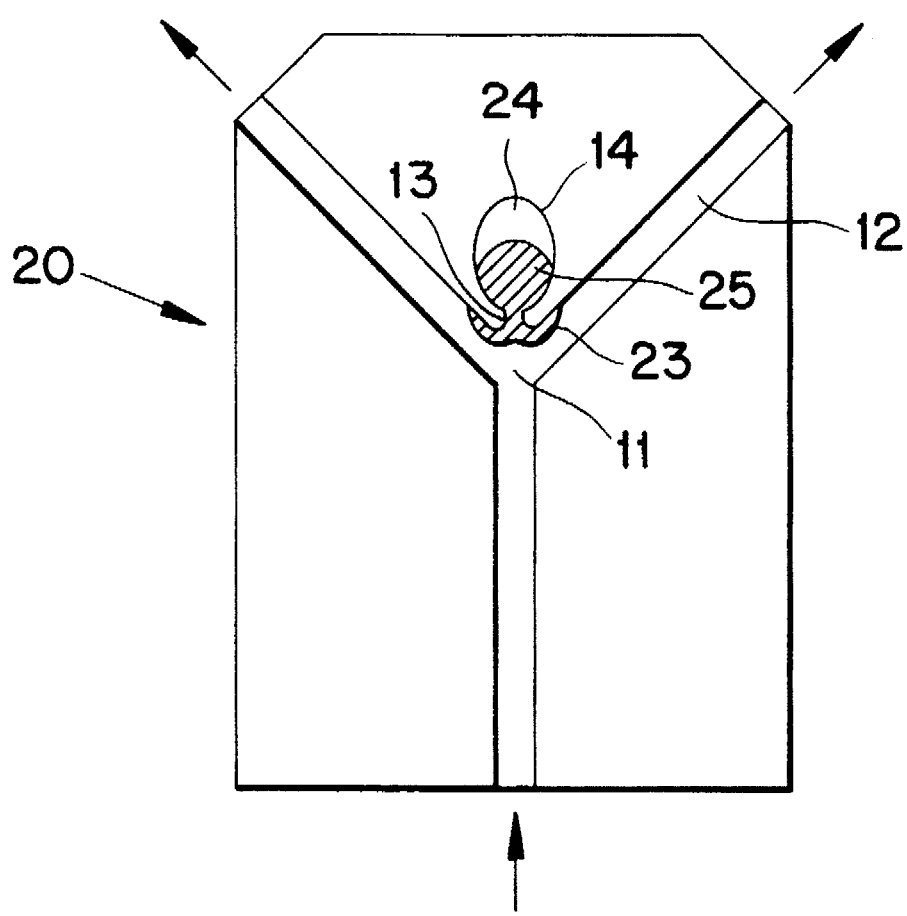
FIG. 4 is a plan view showing enlarged the part of FIG. 3 which is encircled with a dashed line and which contains a Y-shaped blood vessel model.

FIG. 4 is a plan view showing enlarged the model of experimental system that is indicated by 20 in FIG. 3.

The model 20 shown in FIG. 4 was a Y-shaped blood vessel 12 that had a dilaton 14 resembling an aneurysm in shape formed at a branch 14. The blood vessel 12 had an inside diameter of 4.0 mm and the dilation 14 had a maximum size of 5.5 mm. The upstream end of the vascular model 20 was connected to a peristaltic pump 16 (MARK-17 of MED TECK Co.) via a feed pipe (i.d. 5.0 mm) that is indicated by 15 in FIG. 3. The downstream end of the model 20 was connected to a drain pipe 17 for perfusion of physiological saline in a quantity of 104 ml/min at a flow rate of 1.38 cm/sec. A Y-connector 18 was attached to the roller pump side of the feed pipe 15 in such a way that one end of the connector 18 would communicate with the roller pump 16 while the other end was available as a tube insertion port 19. An air vent 21 was provided on the Y-connector side 18 of the feed pipe 15.

The experimental system shown in FIG. 3 was fitted with a polyolefinic tube 22 (i.d. 0.65 mm) that was inserted through the tube insertion port 19 in such a way that its distal end would be directed toward the dilation 14 of the model 20 shown in FIG. 4. The interior of the tube 22 was preliminarily primed with 50 v/v % ethanol. The vascular lesion embolizing material 10 prepared in Example 1 was supplied into the tube 22, which was connected to a syringe 26 charged with 50 v/v % ethanol. By manipulation of the syringe 26, the embolizing material 10 was transported to the dilation 14, in which it was retained.

As soon as it contacted the physiological saline in the dilation, the embolizing material 10 began to swell to close the interior of the dilation. Three minutes after its retention, the embolizing material was found to have closed the interior of the dilation almost completely. Throughout the process of embolization, all part of the high-polymer gel stayed in the dilation 14 without being carried away by water streams. Furthermore, the tube 22 could be easily withdrawn after embolization.

COMPARATIVE EXAMPLE 1

A solution of 10% EVAL® (EP F104 of Kuraray Co., Ltd.) in dimethyl sulfoxide was supplied as a vascular lesion embolizing material through a single lumen tube into the interior of a dilation in the same model as in Example 2 using the same experimental system as in Example 2. As shown in FIG. 4, EVAL® 25 precipitating out of the solution partly obstructed the dilation 14 but, at the same time, EVAL® precipitating out of the excess solution overflowing the neck 13 of the dilation 14 adhered to the inner wall 23 of the branch. The interior of the dilation 14 remained clear and the embolizing material in it would hardly solidify.

While the present invention has been described above specifically with reference to examples, it should be noted that various other embodiments may be contemplated as long as they comply with the object of the present invention.

The present invention offers the following advantages.

First, an embolizing material that comprises a high-polymer gel is used in such a way that the swollen high-polymer gel will obstruct and embolize the blood vessel in a vascular lesion to be treated. Hence, the gel precipitating in the blood vessel will not be disrupted into small pieces, nor will any side effects be caused by solvents. Second, the high-polymer gel is produced by immersing a precipitate in an aqueous salt solution and this insures that the gel, even if it is dried, retains the ability to absorb such a large amount of water as to swell rapidly. Hence, the high-polymer gel can advantageously be used as a material for embolizing the affected part with vascular lesion. The vascular lesion embolizing material of the present invention can be easily passed through a small-diameter tube such as a catheter without causing sticking between the tip of the tube and the inner surface of a blood vessel. In addition, the inserted tube can be withdrawn without exerting any undue force and, hence, there is no need to adopt a cumbersome technique.

Third, the interior of a vascular lesion can be gradually filled with the embolizing material of the present invention in such a way that it builds up in any shape that suits the affected part with lesion. It is also easy to control the volume of the embolizing material to be charged. Furthermore, if a blood coagulating property is imparted to the vascular lesion embolizing material, an in vivo reaction (clot formation) can be caused to achieve efficient occlusion of the affected part with lesion.

Fourthly, alginic acid can be used as a particularly advantageously vascular lesion embolizing material since it is highly safe (as evidenced by its conventional use as a hemorrhage covering material) and because it is biodegradable over time.

Fifthly, an angiographic material or a therapeutic drug may be contained in the high-polymer gel. This not only insures that the vascular lesion embolizing material of the present invention can be supplied to the area of a vascular lesion to be embolized under X-ray monitoring; it also permits satisfactory post-operative management of the patient to provide enhanced therapeutic efficacy.

What is claimed is:

1. A method for treating a vascular lesion using a vascular lesion-embolizing material, said method comprising the steps of:

applying the vascular lesion-embolizing material in the interior of the vascular lesion to bring said embolizing material into contact with blood flowing through the vascular lesion, said vascular lesion-embolizing material comprising a dried water-absorbent polymer gel capable of absorbing water in an amount of at least 10 ml/g when measured by dipping the dry polymer gel in a physiological saline; and allowing said embolizing material to swell thereby completing the embolization of the vascular lesion;

said polymer gel being produced by precipitating a solution containing a water-soluble polymer of an alkali metal salt of alginic acid in a solution containing a polyvalent cation, immersing the resulting precipitate in a salt solution, and then drying the precipitate.

2. The method according to claim 1, wherein said embolizing material further comprises an X-ray contrast medium.

3. The method according to claim 1, wherein said polyvalent cation is a calcium ion.

4. The method according to claim 1, wherein said polymer gel is bound with a binder.

5. The method according to claim 1, wherein said vascular lesion is in a cerebrum, spine, abdominal port or limb.

6. A method for treating a vascular lesion using a vascular lesion-embolizing material, said method comprising the steps of:

applying the vascular lesion-embolizing material in the interior of the vascular lesion to bring said embolizing material into contact with blood flowing through the vascular lesion, said vascular lesion-embolizing material comprising a dried water-absorbent polymer gel capable of absorbing water in an amount of at least 10 ml/g when measured by dipping the dry polymer gel in a physiological saline, and a blood coagulating substance; and allowing said embolizing material to swell thereby completing the embolization of the vascular lesion and, simultaneously, to dissolve said blood coagulating substance thereby coagulating blood absorbed in the swollen embolizing material;

said polymer gel being produced by precipitating a solution containing a water-soluble polymer of an alkali metal salt of alginic acid in a solution containing a polyvalent cation, immersing the resulting precipitate in a salt solution, and then drying the precipitate.

7. The method according to claim 6, wherein said embolizing material further comprises an X-ray contrast medium.

8. The method according to claim 6, wherein said polyvalent cation is a calcium ion.

9. The method according to claim 6, wherein said polymer gel is bound with a binder.

10. The method according to claim 6, wherein said vascular lesion is in a cerebrum, spine, abdominal port or limb.

* * * * *

UNITED STATES PATENT AND TRADEMARK OFFICE
CERTIFICATE OF CORRECTION

PATENT NO. : 5,624,685
DATED : April 29, 1997
INVENTOR(S) : Toru TAKAHASHI et al It is certified that error appears in the above-indentified patent and that said Letters Patent is hereby corrected as shown below:

In Column 2, line 50, after "aneurysm" insert -- to get into the blood vessel will adhere along the blood --.

In Column 8, line 19, delete "1.38" and insert -- 13.8 --.

Signed and Sealed this

First Day of July, 1997

Attest:

BRUCE LEHMAN

Attesting Officer

Commissioner of Patents and Trademarks